(12) United States Patent
Bon et al.

(10) Patent No.: US 6,572,536 B1
(45) Date of Patent: Jun. 3, 2003

(54) AUTOCLAVABLE FLEXIBLE FIBERSCOPE

(75) Inventors: Edwin Bon, Canton, GA (US); Robert Biggs, Marietta, GA (US); Edward J. Lortie, Alpharetta, GA (US)

(73) Assignee: Visionary Biomedical, Inc., Roswell, GA (US)

( * ) Notice: Subject to any disclaimer, the term of this patent is extended or adjusted under 35 U.S.C. 154(b) by 104 days.

(21) Appl. No.: 09/706,234

(22) Filed: Nov. 3, 2000

Related U.S. Application Data

(60) Provisional application No. 60/163,592, filed on Nov. 5, 1999.

(51) Int. Cl.[7] ................................................ A61B 1/04
(52) U.S. Cl. ...................... 600/133; 600/182; 600/176; 600/129; 600/130
(58) Field of Search ........................... 600/133, 176, 600/101, 129, 109, 130, 112, 167, 139, 168, 141, 160, 161, 162, 173, 178, 182; 385/119; 348/73, 75

(56) References Cited

U.S. PATENT DOCUMENTS

| | | | |
|---|---|---|---|
| 4,341,205 A | | 7/1982 | Hosono et al. |
| 4,545,369 A | | 10/1985 | Sato |
| 4,758,222 A | | 7/1988 | McCoy |
| 4,770,163 A | * | 9/1988 | Ono et al. ................... 600/130 |
| 4,878,485 A | | 11/1989 | Adair |
| RE33,854 E | | 3/1992 | Adair |
| 5,151,096 A | | 9/1992 | Khoury |
| 5,160,559 A | | 11/1992 | Scovil et al. |
| 5,188,094 A | | 2/1993 | Adair |
| 5,199,950 A | | 4/1993 | Schmitt et al. |
| 5,217,454 A | | 6/1993 | Khoury |
| 5,313,934 A | * | 5/1994 | Wiita et al. ................. 600/133 |
| 5,342,299 A | | 8/1994 | Snoke et al. |
| 5,349,941 A | | 9/1994 | Hori |
| 5,354,266 A | | 10/1994 | Snoke |
| 5,399,164 A | | 3/1995 | Snoke et al. |
| 5,415,157 A | | 5/1995 | Welcome |
| 5,419,313 A | | 5/1995 | Lemke |
| 5,423,311 A | | 6/1995 | Snoke et al. |
| 5,437,636 A | | 8/1995 | Snoke et al. |
| 5,447,148 A | | 9/1995 | Oneda et al. |
| 5,458,133 A | * | 10/1995 | Yabe et al. .................. 600/133 |
| 5,489,256 A | | 2/1996 | Adair |
| 5,490,845 A | | 2/1996 | Racz |
| 5,494,483 A | * | 2/1996 | Adair .......................... 600/130 |
| 5,496,269 A | | 3/1996 | Snoke |
| 5,526,820 A | | 6/1996 | Khoury |
| 5,531,687 A | | 7/1996 | Snoke et al. |
| 5,538,496 A | | 7/1996 | Yabe et al. |
| 5,542,924 A | | 8/1996 | Snoke et al. |
| 5,599,278 A | | 2/1997 | Hibbard |
| 5,624,397 A | | 4/1997 | Snoke et al. |
| 5,630,782 A | | 5/1997 | Adair |
| 5,634,881 A | | 6/1997 | Francis |
| 5,643,175 A | | 7/1997 | Adair |
| 5,810,713 A | | 9/1998 | Rondeau et al. |
| 5,810,788 A | | 9/1998 | Racz |
| 5,830,127 A | | 11/1998 | DeCastro |
| 5,846,221 A | | 12/1998 | Snoke et al. |
| 5,857,996 A | | 1/1999 | Snoke |
| 5,860,913 A | * | 1/1999 | Yamaya et al. .............. 600/129 |
| 5,860,953 A | | 1/1999 | Snoke et al. |
| 5,868,665 A | * | 2/1999 | Biggs .......................... 600/112 |
| 5,899,891 A | | 5/1999 | Racz |
| 6,019,719 A | * | 2/2000 | Schulz et al. ............... 600/129 |
| 6,030,339 A | * | 2/2000 | Tatsuno et al. .............. 600/112 |
| 6,030,360 A | * | 2/2000 | Biggs .......................... 600/139 |
| 6,146,326 A | * | 11/2000 | Pollack et al. .............. 600/141 |
| 6,146,355 A | | 11/2000 | Biggs |
| 6,213,974 B1 | * | 4/2001 | Smith et al. ................. 600/139 |

* cited by examiner

Primary Examiner—Teresa Walberg
Assistant Examiner—Fadi H. Dahbour
(74) Attorney, Agent, or Firm—Gardner Groff, P.C.

(57) ABSTRACT

An autoclavable flexible fiberscope for remote visualization. A flexible fiberscope shaft including a number of flexible fiberoptic image-transmitting fibers is attached to a video coupler for connection to a video camera or other external video device. High-temperature materials of fabrication and high-temperature seals are provided to resist damage during autoclave sterilization.

15 Claims, 3 Drawing Sheets

AUTOCLAVABLE FLEXIBLE FIBERSCOPE

CROSS-REFERENCE TO RELATED APPLICATION

This application claims the benefit of U.S. Provisional Patent Application Ser. No.: 60/163,592, filed Nov. 5, 1999, the entire scope and content of which application is hereby incorporated herein by reference.

BACKGROUND OF THE INVENTION

1. Field of the Invention

The present invention relates generally to medical devices and procedures, and more particularly to a flexible fiberscope or endoscope that is constructed to withstand sterilization by autoclaving.

2. Description of Related Art

Medical practitioners often utilize fiberoptic endoscopes (interchangeably referred to herein as "fiberscopes", "endoscopes", "arthroscopes", "laparoscopes", etc.) in the performance of a variety of medical procedures. For example, fiberscopes in various forms are utilized with human or animal patients in arthroscopic procedures, laparoscopic procedures, cardiology, and diagnosis and treatment within the epidural space. Fiberscopes typically comprise a bundle of glass or other optical image transmission fibers, and one or more lenses for collecting and focusing an image. Flexible and rigid fiberscopes are known.

For economic reasons, it is typically desirable to reuse a fiberscope for more than one procedure. During use, however, the fiberscope typically becomes contaminated and must be cleaned and sterilized prior to reuse. A preferred method of sterilization of surgical implements is by way of exposure to elevated temperatures in an autoclave. While autoclavable rigid fiberscopes are known, it has proven difficult to produce a flexible fiberscope capable of withstanding sterilization by autoclave.

Accordingly, it has been found desirable to provide a flexible fiberscope capable of withstanding repeated autoclave sterilization. It is to the provision of an autoclavable flexible fiberscope meeting this and other needs that the present invention is primarily directed.

SUMMARY OF THE INVENTION

The present invention provides an autoclavable flexible fiberscope for optical image transmission. The autoclavable flexible fiberscope of the present invention can be adapted to use with a variety of medical procedures. In example embodiments, the autoclavable flexible fiberscope of the present invention is adapted for insertion into a lumen of a delivery vehicle such as a steerable catheter.

In one aspect, the invention is a fiberscope including a lens, a fiberoptic imaging bundle having a proximal end and a distal end, and a heat-resistant retaining sleeve mechanically coupling the lens to the distal end of the fiberoptic imaging bundle.

In another aspect, the invention is a video coupler for a fiberscope. The video coupler includes a scope coupling for connection to a fiberscope, a lens assembly including at least one lens, and high-temperature sealing means for isolating the lens assembly from an external environment.

In yet another aspect, the invention is a fiberscope and video coupling system including a fiberscope having a lens, a flexible fiberoptic imaging bundle having a proximal end and a distal end, a heat-resistant retaining sleeve mechanically coupling the lens to the distal end of the fiberoptic imaging bundle, and a scope housing including a bore engaging the proximal end of the imaging bundle. The fiberscope also includes a video coupler having a scope coupling for connection to the scope housing, a lens assembly including at least one lens, and high-temperature sealing means for isolating the lens assembly from an external environment.

These and other features and advantages of the present invention are described herein with reference to example embodiments shown in the appended drawing figures.

BRIEF DESCRIPTION OF THE DRAWING FIGURES

DETAILED DESCRIPTION

Figure 1:
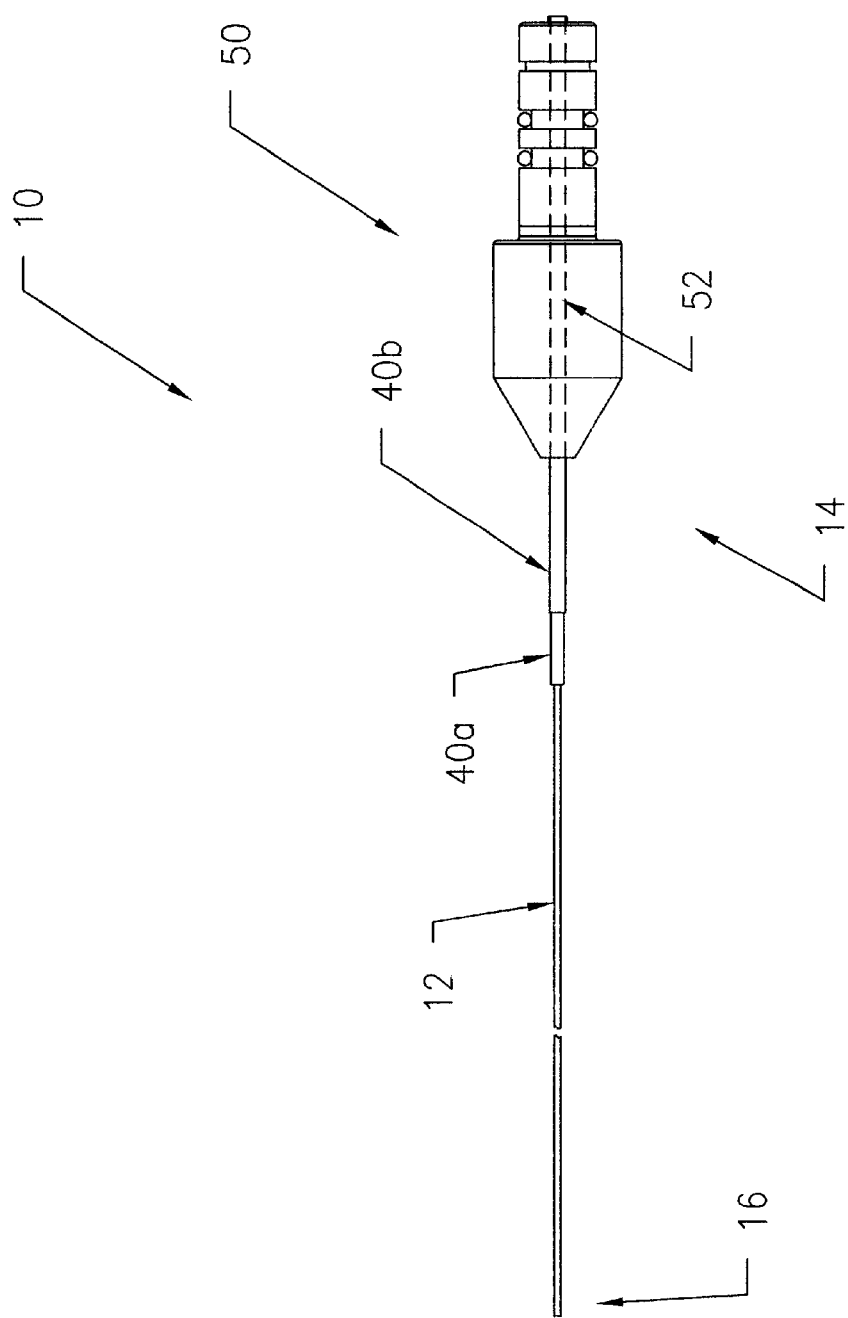
FIG. 1 shows a side view, in partial cross-section, of a fiberscope according to a preferred form of the present invention.
Figure 2:
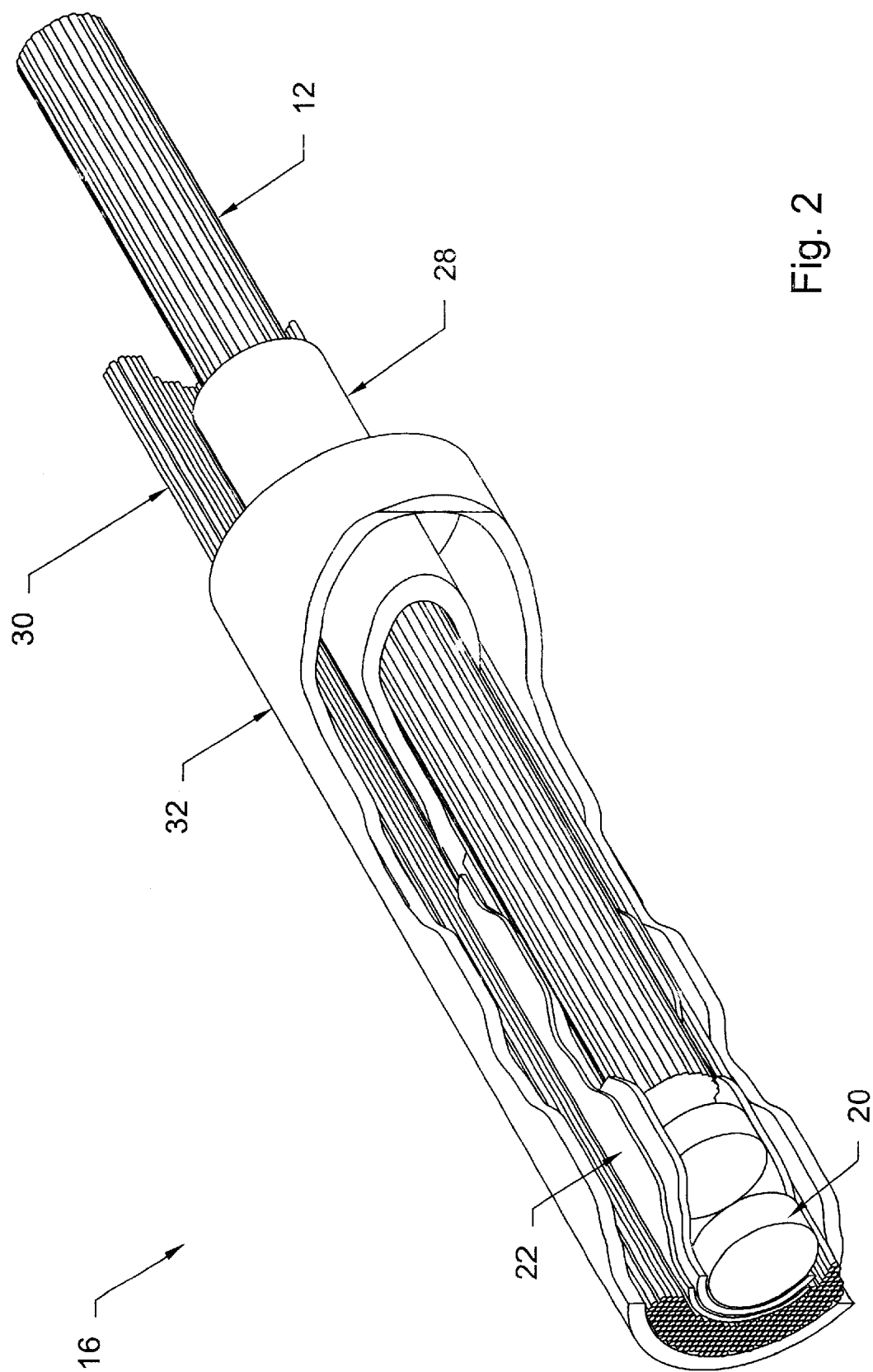
FIG. 2 is a perspective view, in partial cutaway, of a distal tip segment of the fiberscope of FIG. 1, according to a preferred form of the present invention.
Figure 3:
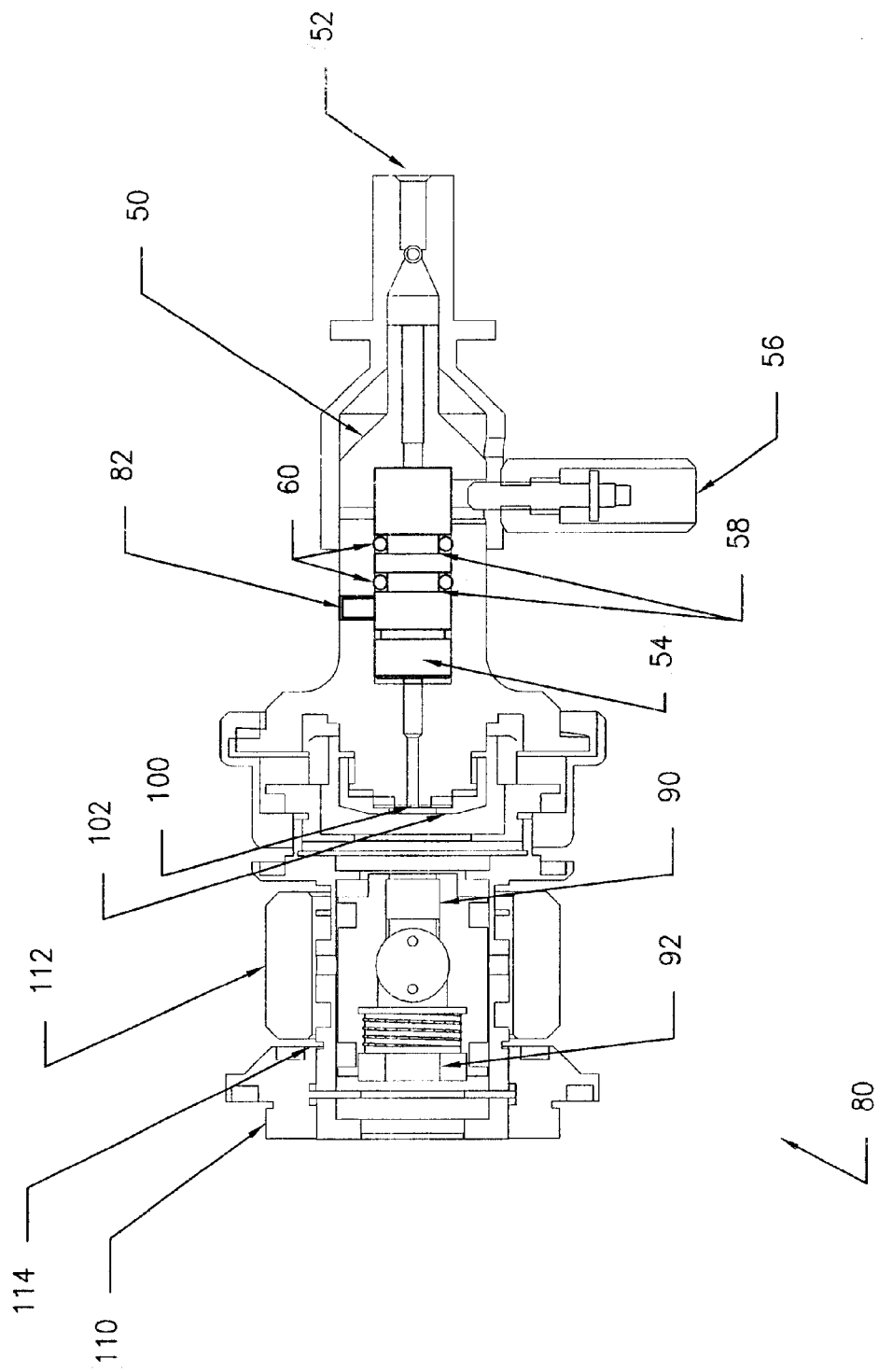
FIG. 3 is a cross-sectional side view of a scope housing and video coupler according to a preferred form of the present invention.

Referring now to the drawing figures, wherein like reference numerals represent like parts throughout, preferred forms of the present invention will now be described. FIGS. 1–3 depict various components of a fiberscope and video coupling system of the present invention. As will be better understood with reference to the disclosure herein, the materials of fabrication of the fiberscope and video coupling system of the present invention are selected to withstand the temperature, pressure, moisture and chemical effects of autoclave sterilization. The components of the fiberscope and video coupling system of the present invention are constructed to minimize or avoid detrimental effect by thermal expansion differential between adjacent components of dissimilar materials.

FIGS. 1 and 2 depict a fiberscope 10 according to a preferred form of the present invention. The fiberscope 10 preferably comprises a flexible fiberoptic imaging bundle 12, comprising a plurality of optically-transmissive flexible glass fibers. The fiberoptic imaging bundle 12 is preferably capable of withstanding temperatures up to at least about 275° F.–302° F. The flexible fiberoptic imaging bundle 12 has a proximal end 14 and a distal end or tip 16.

The distal end 16 is shown in greater detail in FIG. 2 according to a preferred form of the invention. The fiberscope 10 preferably further comprises an imaging lens 20, formed of optical grade glass or high-temperature plastic. In preferred form, the lens 20 and imaging bundle 12 are coupled by mechanical means only. For example, in a particularly preferred embodiment of the invention, the lens 20 and the distal end 16 of the imaging bundle 12 are coupled by a heat-resistant retaining sleeve 22. The retaining sleeve 22 preferably comprises a stainless steel sleeve housing adapted to surround and tightly engage the distal end 16 of the imaging bundle 12 and the lens 20 to securely couple the lens to the imaging bundle.

The fiberscope 10 of the present invention preferably further comprises a protective image bundle sheath 28 enclosing the lens 20, the retaining sleeve 22, and at least a portion of the imaging bundle 12. In preferred form, the protective sheath 28 comprises a braided polyimide flexible sheathing material. The protective sheath 28 is preferably pulled over the entire length of the retaining sleeve 22 and the imaging bundle 12, to totally encase the flexible shaft portion of the fiberscope 10. The outer surface of the retaining sleeve 22 is preferably continuously glued to the inner diameter of the distal tip end of the protective sheathing 28, using a high-temperature epoxy or other high-temperature adhesive sealant, to form a continuous seal therebetween.

The fiberscope 10 of the present invention preferably further comprises one or more light fibers 30 for transmitting light from an illumination source (unshown) to the distal end 16 of the fiberscope 10 for illumination of the target tissue or other object to be observed. The light fibers 30 preferably comprise flexible glass fiberoptic fibers. An outer protective sheath 32 preferably encases the light fibers 30 and the imaging bundle 12 and lens 20 assembly within the protective sheath 28. The outer protective sheath 32 preferably comprises a temperature-resistant, braided polyimide flexible sleeve. A high-temperature epoxy or other sealant is preferably provided between the protective sheath 28 and the outer protective sheath 32 to form a continuous seal therebetween.

The fiberscope 10 of the present invention preferably further comprises one or more strain-relief sleeves 40 at the proximal end 14 of the imaging bundle 12. Two strain-relief sleeves 40a, 40b are depicted in FIG. 1. Inner strain relief 40a encases the proximal end 14 of the imaging bundle 12 and outer strain relief sleeve 40b encases at least a portion of the inner strain relief sleeve. The strain relief sleeve(s) 40 preferably comprise a segment of heat-shrinkable tubing. The segment(s) of heat-shrinkable tubing are positioned onto the proximal end 14 of the fiberoptic imaging bundle 12, and an appropriate amount of heat is applied thereto, causing the tubing to shrink and tightly encase and engage the imaging bundle 12 and/or any inner strain relief sleeve (s).

The fiberscope 10 of the present invention preferably further comprises a scope housing 50 engaging the proximal end 14 of the imaging bundle 12. The scope housing 50 preferably comprises a body formed of aluminum, Ultem™ (by G.E. Plastics Structured Products, of Pittsfield, Mass.), or other high-temperature, substantially rigid material. The scope housing 50 preferably defines a bore 52 extending substantially therethrough, generally along its central, longitudinal axis. The bore 52 preferably comprises internal threads or surface features adapted to securely engage the proximal end 14 of the flexible fiberoptic imaging bundle 12. A high-temperature epoxy or other high-temperature adhesive preferably secures the proximal end 14 of the imaging bundle 12 within the bore 52 of the scope housing 50. The proximal end 14 of the imaging bundle 12 preferably extends substantially entirely through the scope housing 50, and most preferably extends slightly beyond the proximal end 54 of the scope housing 50. The proximal end 14 of the imaging bundle 12 is preferably polished to produce a satisfactory image.

The scope housing 50 preferably further comprises a locking screw 56 threadedly engaged within a cooperating bore formed in the scope housing. The locking screw 56 provides a position adjustment and locking mechanism for axial positioning of the fiberscope 10 within a delivery vehicle such as a steerable catheter (unshown). The locking screw 56 preferably engages a slotted docking member of the delivery vehicle, whereby the fiberscope 10 is longitudinally positioned by sliding the locking screw 56 within the slotted docking member to a desired scope position, and the scope is locked in position by tightening the locking screw against the docking member.

The proximal end 54 of the scope housing 50 preferably comprises a generally cylindrical outer surface for coupling with a video coupler, described in greater detail below. One or more circumferential O-ring grooves 58 are preferably provided in the outer surface of the proximal end 54 of the scope housing 50, and a high-temperature O-ring 60 is preferably installed within each O-ring groove.

The present invention preferably further comprises a video relay coupling or video coupler 80 for coupling the fiberscope to a video relay module (VRM), a video camera head, an eyepiece, and/or other external video device(s). The video coupler preferably comprises a quick-connect-and-release bayonet coupling for connection to the video device. The video coupler preferably further comprises a scope coupling for connection to the proximal end 54 of the scope housing 50. The video coupler 80 preferably comprises a coupler body formed from aluminum, Ultem™, or other high-temperature-resistant material of construction. In a further preferred form, the scope coupling of the video coupler 80 comprises a generally cylindrical internal bore adapted to receive the proximal end 54 of the scope housing 50. The O-ring(s) 60 mounted to the scope housing 50 sealingly engage the inner surface of the bore of the video coupler 80 to form a continuous seal therebetween. Most preferably, a double O-ring seal is provided, as seen best with reference to FIG. 3. The video coupler 80 is preferably releasably coupled to the scope housing 50 by means of one or more set screws 82 or other retention means.

The video coupler 80 of the present invention preferably further comprises a lens assembly including at least one optical lens. In the depicted embodiment of FIG. 3, the video coupler 80 preferably comprises a first lens 90 and a second lens 92. A series of spacers and retaining rings are preferably provided for securing the lenses in place within the video coupler 80, as seen best with reference to FIG. 3.

In preferred form, the video coupler 80 of the present invention preferably further comprises a high-temperature sealing means for isolating the lens assembly from the external environment. For example, the high-temperature sealing means isolates the more temperature-sensitive internal components of the lens assembly from the potentially damaging environment of the autoclave during autoclave sterilization. The high-temperature sealing means preferably comprises at least one high-temperature-resistant window, formed of a generally transparent, temperature-resistant material such as, for example, optical grade glass, fused silica, and/or borosilicate. The window 100 is preferably secured in place on the video coupler 80 by means of a window retainer 102. A high temperature resistant O-ring 104 is preferably provided to form a heat-resistant seal between the window 100 and the outer body of the video coupler 80, thereby isolating the lens assembly and other internal components of the video coupler 80 from the external environment.

The video coupler 80 preferably further comprises a camera adapter 110 for releasable connection to a video camera (unshown). A focus ring 112 and bearing ring 114 are preferably provided on the video coupler 80 for focusing the image transmitted thereby. As seen best with reference to FIG. 3, all interfaces between components of the video coupler are preferably continuously sealed by high-temperature O-rings and/or high temperature epoxy.

The fiberscope 10 and video coupler 80 preferably cooperate to form a fiberscope and video coupling system. The fiberscope and video coupling system of the present invention is assembled by mating the proximal end 54 of the scope housing 50 into the bore of the video coupler 80. The components are preferably semi-permanently connected by means of a threaded connection therebetween. The O-ring(s) 60 seal the interface between the video coupler 80 and the scope housing 50 against the temperature, pressure, moisture, and chemical effects of autoclave sterilization.

While the invention has been described in its preferred forms, it will be readily apparent to those of ordinary skill in the art that many additions, modifications and deletions can be made thereto without departing from the spirit and scope of the invention.

What is claimed is:

1. A fiberscope comprising:
    a lens;
    a flexible fiberoptic imaging bundle having a proximal end and a distal end;
    a heat-resistant retaining sleeve mechanically coupling said lens to the distal end of said fiberoptic imaging bundle; and
    a protective sheath enclosing said lens, at least a portion of said imaging bundle, and said retaining sleeve, wherein said protective sheath comprises a braided polyimide sheath.

2. A fiberscope comprising:
    a lens;
    a flexible fiberoptic imaging bundle having a proximal end and a distal end;
    a heat-resistant retaining sleeve mechanically coupling said lens to the distal end of said fiberoptic imaging bundle;
    a protective sheath enclosing said lens, at least a portion of said imaging bundle, and said retaining sleeve; and
    a high-temperature epoxy bonding said protective sheath to said retaining sleeve.

3. A fiberscope comprising:
    a lens;
    a flexible fiberoptic imaging bundle having a proximal end and a distal end;
    a heat-resistant retaining sleeve mechanically coupling said lens to the distal end of said fiberoptic imaging bundle;
    a protective sheath enclosing said lens, at least a portion of said imaging bundle, and said retaining sleeve, and
    a strain-relief sleeve comprising heat-shrinkable tubing surrounding at least a proximal portion of said imaging bundle.

4. A fiberscope comprising:
    a lens;
    a flexible fiberoptic imaging bundle having a proximal end and a distal end;
    a heat-resistant retaining sleeve mechanically coupling said lens to the distal end of said fiberoptic imaging bundle;
    a scope housing comprising a bore receiving the proximal end of said imaging bundle, wherein said scope housing comprises an O-ring coupling for connection to a video coupler.

5. A fiberscope comprising:
    a lens;
    a flexible fiberoptic imaging bundle having a proximal end and a distal end;
    a heat-resistant retaining sleeve mechanically coupling said lens to the distal end of said fiberoptic imaging bundle; and
    a scope housing comprising a bore receiving the proximal end of said imaging bundle, wherein said scope housing comprises a position adjustment and locking mechanism for axial positioning of said fiberscope within a delivery vehicle.

6. A video coupler for a fiberscope, said video coupler comprising:
    a scope coupling for connection to a fiberscope;
    a lens assembly comprising at least one lens;
    high-temperature sealing means for isolating said lens assembly from an external environment; and
    a video relay coupling for connection to an external video device, wherein said video relay coupling comprises a quick-connect bayonet coupling.

7. A video coupler for a fiberscope, said video coupler comprising:
    a scope coupling for connection to a fiberscope;
    a lens assembly comprising at least one lens; and
    high-temperature sealing means for isolating said lens assembly from an external environment, wherein said high-temperature sealing means comprises an aluminum body, at least one high temperature-resistant window, and at least one O-ring seal.

8. A fiberscope and video coupling system comprising:
    a fiberscope comprising a lens, a flexible fiberoptic imaging bundle having a proximal end and a distal end, a heat-resistant retaining sleeve mechanically coupling said lens to the distal end of said fiberoptic imaging bundle and a scope housing comprising a bore engaging the proximal end of said imaging bundle; and
    a video coupler comprising a scope coupling for connection to said scope housing, a lens assembly comprising at least one lens, and high-temperature sealing means for isolating said lens assembly from an external environment.

9. The fiberscope and video coupling system of claim 8, further comprising a protective sheath enclosing said lens, at least a portion of said imaging bundle, and said retaining sleeve, wherein said protective sheath comprises a braided polyimide sheath.

10. The fiberscope and video coupling system of claim 8, further comprising a strain-relief sleeve comprising heat-shrinkable tubing surrounding at least a proximal portion of said imaging bundle.

11. The fiberscope and video coupling system of claim 8, further comprising an O-ring coupling between said video coupler and said scope housing.

12. The fiberscope and video coupling system of claim 8, further comprising a position adjustment and locking mechanism for axial positioning of said system within a delivery vehicle.

13. The fiberscope and video coupling system of claim 8, wherein said video coupler comprises a video relay coupling for connection to an external video device.

14. The fiberscope and video coupling system of claim 13, wherein said video relay coupling comprises a quick-connect bayonet coupling.

15. The fiberscope and video coupling system of claim 13, wherein said high-temperature sealing means comprises an aluminum body, at least one high temperature-resistant window, and at least one O-ring seal.

* * * * *